United States Patent [19]

Paul et al.

[11] 4,115,572

[45] Sep. 19, 1978

[54] IMIDAZO-[1,5-D]-AS-TRIAZIN-1(2H)-ONES AND METHOD OF AMELIORATING ASTHMA

[75] Inventors: Rolf Paul, River Vale, N.J.; Judith Menschik, Tappan, N.Y.

[73] Assignee: American Cyanamid Company, Stamford, Conn.

[21] Appl. No.: 843,302

[22] Filed: Oct. 18, 1977

Related U.S. Application Data

[63] Continuation-in-part of Ser. No. 765,337, Feb. 3, 1977, abandoned.

[51] Int. Cl.$^2$ .............................................. C07D 471/04
[52] U.S. Cl. ..................................... 424/249; 544/184
[58] Field of Search .......................... 544/184; 424/249

[56] References Cited

U.S. PATENT DOCUMENTS 3,840,537  10/1974  Garside et al. ........................ 544/184

Primary Examiner—John M. Ford
Attorney, Agent, or Firm—Harry H. Kline

[57] ABSTRACT

There are provided substituted imidazo[1,5-d]-as-triazin-1(2H)-ones useful as anti-asthmatic agents.

14 Claims, No Drawings

IMIDAZO-[1,5-D]-AS-TRIAZIN-1(2H)-ONES AND METHOD OF AMELIORATING ASTHMA

This application is a continuation-in-part of our co-pending application Ser. No. 765,337, filed on Feb. 3, 1977, now abandoned.

BRIEF SUMMARY OF THE INVENTION

This invention relates to new organic compounds and, more particularly, is concerned with novel substituted imidazo[1,5-d]-as-triazin-1(2H)-ones which may be represented by the following structural formula:

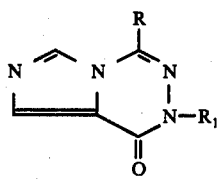

wherein R is hydrogen or alkyl having up to 6 carbon atoms and $R_1$ is hydrogen or allyl. The invention also includes novel composition of matter contining the above defined compounds and the method of meliorating asthma in mammals therewith.

DETAILED DESCRIPTION OF THE INVENTION

The novel compounds of the present invention are generally obtainable as white to yellow crystalline materials having characteristic melting points and absorption spectra and which may be purified by recrystallization from common organic solvents such as methanol, ethanol, dimethylformamide, chloroform, and the like. They are appreciably soluble in non-polar organic solvents such as diphenyl ether but are relatively insoluble in water.

The novel compounds of the present invention where $R_1$ is hydrogen as hereinabove defined may be readily prepared in accordance with the following reaction scheme:

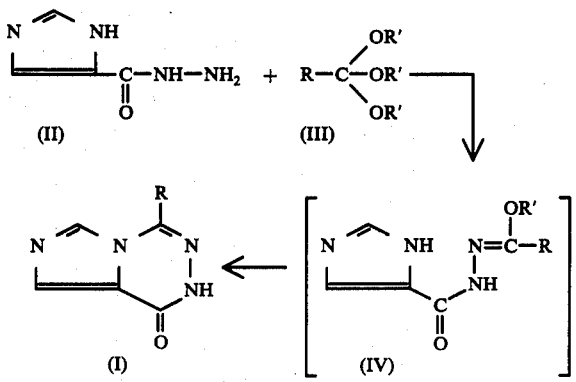

wherein R' is methyl or ethyl, R and $R_1$ are as hereinabove defined. In accordance with this reaction scheme, 4-imidazolecarboxylic acid hydrazide (II) is condensed with an alkyl orthoformate (R is hydrogen in III) or an orthoester of an alkanoic acid (R is alkyl in III) to provide the intermediates (IV) which are not isolated. This condensation is conveniently carried out in a lower alkanol solvent at the reflux temperature thereof for a period of time of from a few hours to 12 hours or more. Cyclization of the intermediates (IV) is readily accomplished by heating in a non-polar high boiling organic solvent such as diphenyl ether at 225°-275° C. for 15-30 minutes whereby the corresponding imidazo-[1,5-d]-as-triazin-1(2H)-ones (I) are obtained.

The final products (I) which are isolated by well known methods, can be further reacted with an alkyl halide, such as allyl chloride or allyl bromide, utilizing well known alkylating procedures to replace the hydrogen with allyl as the $R_1$ substituent in the hereinabove identified novel compounds.

The novel compounds of the present invention possess anti-asthma activity at non-toxic doses and as such are useful as anti-asthmatic agents. Anti-asthma activity was determined by the mouse passive cutaneous anaphylaxis (PCA) test as follows.

Preparation of Mouse Immunoglobulins, IgE and IgG

Female mice (Charles River Breeding Labs.), weighing 20-22 gm. are inoculated intraperitoneally at approximately 3 weeks of age with 0.5 ml. of Timothy pollen antigen in complete Freund's adjuvant. The sensitizing antigen is prepared by suspending 60 mg. of Timothy antigen (Phleum pratense) in 6 ml. of Freund's Complete Adjuvant (Difco Labs.). Approximately 3-5 weeks after inoculation, ascitic fluid is removed from responding mice and tested for IgE and IgG type antibody by mouse PCA as follows:

Samples of ascitic fluid are diluted 1:10 and 50 μl are injected intradermally into five mice. The mice are challenged intravenously with antigen and Evans blue dye 48 hours later. Fifteen minutes after challenge, the dorsal skin is removed and examined for blue spots. Samples of ascitic fluid with IgE-type activity are pooled and titered to determine the dilution which gives a PCA lesion (area of blue) slightly greater than one centimeter in diameter. This dilution (typically 1:10) is then used routinely for that pool of fluid. To test for IgG activity, the ascitic fluid is diluted 1:40, 50 μl is injected intradermally and intravenous challenge is made 2 hours later. Samples of ascitic fluid with IgG type activity are pooled, heated at 56° C. for 4 hours and titered to obtain a PCA lesion slightly greater than one centimeter in diameter (Typically 1:40).

Passive Cutaneous Anaphylaxis Test

At −50 hour (relative to antigen challenge at 0 hour) 50 μl of IgE is injected intradermally on the left side of a 25 gm. female mouse, posterior to the axilla at the level of the diaphragm. At −2 hour, 50 μl of IgG is injected intradermally on the right side of the mouse. The mice are then placed in individual cages and randomly assigned to control or treatment groups. Challenge and reading are performed in serial order so that reading of the assay is essentially blind. At −1 hour, the control animals received an intraperitoneal injection of 0.5 ml. of a 0.05% solution of carboxymethylcellulose in saline. For treatment animals, the test compound is dissolved or suspended in the carboxymethylcellulose-saline solution and administered intraperitoneally at −1 hour at 50 mg./kg. At 0 hour, the mice are anesthetized with ether and 0.5 ml. of saline containing 0.5 mg. of Timothy antigen and 2.5 mg. of Evans blue dye is injected into the tail vein. At +15 minutes the mice are sacrificed by cervical dislocation, the dorsal skin is removed and the blue PCA spots are examined on the inside surface. The largest and smallest diameters of the lesion and a qualitative estimate of intensity of color are recorded. The mean of the products of diameters (area) for mice in a given treatment group are compared with the control group. IgE and IgG lesions are analyzed independently. If the area for a treatment group is significantly smaller than the lesion area for the control group for either IgE or IgG lesion, the test compound is considered to be active as an anti-asthma agent. The results with a typical compound of this invention appear in Table I below.

TABLE I

| COMPOUND | MOUSE PCA TEST |
|---|---|
| Imidazo[1,5-d]-as-triazin-1(2H)-one | Accept |
| 4-n-Propyl imidazo[1,5-d]-as-triazin-1(2H)-one | Accept |

The novel compounds of the present invention have thus been found to be highly useful for meliorating asthma in mammals when administered in amounts ranging from about 1.0 milligram to about 25.0 mg. per kilogram of body weight per day. A preferred dosage regimen for optimum results would be from about 5.0 mg. to about 15.0 mg. per kilogram of body weight per day, and such dosage units are employed that a total of from about 0.35 gram to about 1.0 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes, and also by inhalation therapy including aerosol sprays.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

Imidazo[1,5-d]-as-triazin-1(2H)-one

A mixture of 6.30 gm. of imidazole-4-carboxylic acid hydrazide [Jones et al., J.A.C.S. 71, 2444 (1949)], 63 ml. of triethyl orthoformate and 500 ml. of ethanol is stirred and refluxed for 8½ hours. The mixture is concentrated in vacuo to a solid. A 100 ml. portion of diphenyl ether is added and the mixture is heated at 240° C. for 15 minutes. The mixture is cooled to room temperature, petroleum ether is added and a solid is collected. This solid is boiled with 150 ml. of methanol. The insoluble portion is collected by filtration and saved. The filtrate is evaporated to give a solid which is heated with 100 ml. of diphenyl ether at reflux for 15 minutes. Cooling to room temperature and the addition of petroleum ether produces a solid. This solid is combined with the above solid, boiled with 600 ml. of methanol and treated with charcoal. The mixture is filtered. The filtrate is boiled down to 35 ml. and cooled giving a solid. This solid is boiled with 50 ml. of ethanol and the hot mixture is filtered. The solid is boiled with 200 ml. of methanol and the insoluble solid is collected by filtration and saved. The filtrate is boiled down to 75 ml. and cooled giving a second solid. These two solids are combined giving the desire product, m.p. 294°–305° C.

EXAMPLE 2

4-n-Propyl-imidazo[1,5-d]-as-triazin-1(2H)-one

A mixture of 3.8 gm. of imidazole-4-carboxylic acid hydrazide, 30 ml. of trimethyl orthobutyrate and 150 ml. of ethanol is refluxed overnight. The mixture is evaporated giving a solid which is washed with petroleum ether and filtered. This solid is combined with 100 ml. of diphenyl ether and heated at 240°–250° C. for 15 minutes. The mixture is cooled, petroleum ether is added and the mixture is filtered. The solid is triturated with hot petroleum ether and filtered giving the desired product, m.p. 116°–117° C.

In repeating the procedure of Example 2 in every detail except there is substituted tri-n-hexyl orthopropionate for trimethyl orthobutyrate, 4-n-hexyl-imidazo[1,5-d]-as-triazin-1(2H)-one is obtained in good yield and purity.

EXAMPLE 3

4-Ethyl-imidazo[1,5-d]-as-triazin-1(2H)-one

The procedure of Example 2 is repeated substituting an equimolecular amount of triethyl orthopropionate for the trimethyl orthobutyrate employed in that example. There is thus obtained the title compound in equally good yield.

EXAMPLE 4

3-N-Allyl-4-n-propyl-imidazo[1,5-d]-as-triazin-1(2H)-one

To a solution of 4-n-propyl-imidazo[1,5-d]-as-triazin-1(2H)-one (0.01 mol) in dimethylformamide (50 ml) is added sodium methoxide (0.01 mol) followed by the addition of allyl bromide (0.012 mol). The reaction mixture is stirred at 20° C. for 16 hours, then heated at 40° C. for 45 minutes, cooled and poured on a mixture of ice and dilute hydrochloric acid. The product is isolated by extraction with chloroform and evaporation. It is purified by recrystallization from cyclohexane or a cyclohexane-benzene mixture; or by silica gel dry column chromatography in chloroform.

EXAMPLE 5

| Preparation of 50 mg. Tablets | | |
|---|---|---|
| Per Tablet | | Per 10,000 Tablets |
| 0.050 gm. | 4-Ethyl-imidazo [1,5-d]-as-triazin-1(2H)-one | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.002 gm. | Magnesium Stearate (1%) | 15 gm. |

The 4-ethyl-imidazo[1,5-d]-as-triazin-1(2H)-one, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 6

| Preparation pf Oral Suspension | |
|---|---|
| Ingredient | Amount |
| 4-n-Propyl-imidazo[1,5-d]-as-triazin-1(2H)-one | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The sorbitol solution is added to 40 ml. of distilled water and the 4-n-propyl-imidazo[1,5-d]-as-triazin-1(2H)-one is suspended therein. The saccharin, sodium benzoate, flavor and dye are added and dissolved. The volume is adjusted to 100 ml. with distilled water. Each ml. of syrup contains 5 mg. of 4-n-propyl-imidazo[1,5-d]-as-triazin-1(2H)-one.

EXAMPLE 7

Preparation of Parenteral Solution

In a solution of 700 ml. of propylene glycol and 200 ml. of water for injection is suspended 20.0 grams of imidazo[1,5-d]-as-triazin-1(2H)-one with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 8

| Preparation of Aerosol Spray | |
|---|---|
| A suspension is prepared of: | |
| 4-Isopropyl-imidazo[1,5-d]-as-triazin-1(2H)-one; micronized (0.5–5.0 microns) | 400 mg. |
| Dichlorodiflurormethane | 100 ml. |
| Sorbitan trioleate | 6.9 mg. |

The active ingredient and sorbitan trioleate are placed in a beaker and the dichlorodifluoromethane is added at −40° C. whereupon a suspension is formed. The mixture is sonified, that is, treated with a Sonifier manfactured by the Branson Sonic Power Co. of Danbury, Conn. as model LS-75 at a current input of 9 amperes for 2 minutes. Additional cold dichlorodifluoromethane is added as necessary to keep the volume at 100 ml. The mixture is uniformily dispersed and has increased stability resulting from the sonification. Each of six 19 ml. stainless steel containers are filled with 15 ml. of the cold mixture, then valves are inserted and sealed in place. On warming, after storage, the 4-isopropyl-imidazo[1,5-d]-as-triazin-1(2H)-one remains dispersed and, after merely casual shaking, gives uniform doses of finely divided drug.

We claim:

1. A compound of the formula:

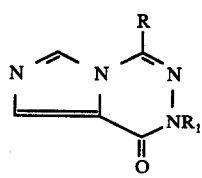

wherein R is selected from the group consisting of hydrogen and alkyl having up to six carbon atoms, and $R_1$ is hydrogen or allyl.

2. The compound according to claim 1 wherein R is hydrogen.

3. The compound according to claim 1 wherein R is methyl.

4. The compound according to claim 1 wherein R is ethyl.

5. The compound according to claim 1 wherein R is n-propyl.

6. The compound according to claim 1 wherein R is isopropyl.

7. The compound according to claim 1 wherein R is n-butyl.

8. The compound according to claim 1 wherein R is tert-butyl.

9. The compound according to claim 1 wherein R is n-hexyl.

10. The compound according to claim 1 wherein $R_1$ is allyl.

11. The method of meliorating asthma in a mammal which comprises administering internally to said mammal an effective amount of a compound of the formula:

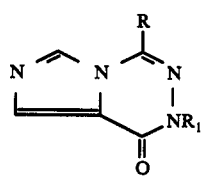

wherein R is selected from the group consisting of hydrogen and alkyl having up to six carbon atoms, and $R_1$ is hydrogen or allyl.

12. A therapeutic composition in dosage unit form useful for meliorating asthma in mammals comprising from about 1.0 mg. to about 25.0 mg. per kg. of body weight per daily dosage unit, in association with a pharmaceutical carrier, of a compound of the formula:

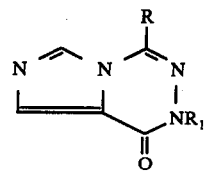

wherein R is selected from the group consisting of hydrogen and alkyl having up to six carbon atoms, and $R_1$ is hydrogen or allyl.

13. The process of preparing compounds of the formula:

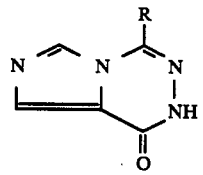

wherein R is selected from the group consisting of hydrogen and alkyl having up to six carbon atoms, which comprises heating a compound of the formula:

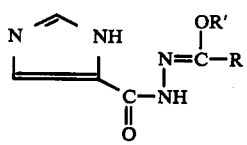

wherein R' is methyl or ethyl and R is as hereinabove defined in a non-polar high boiling organic solvent at a temperature of 225°–275° C. for a period of time sufficient for a substantial degree of ring closure to occur.

14. The process of preparing compounds of the formula:

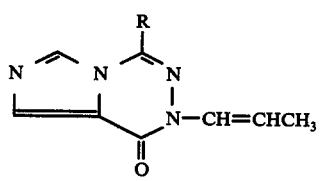

(I)

wherein R is selected from the group consisting of hydrogen and alkyl having up to six carbon atoms, which comprises heating a compound of the formula:

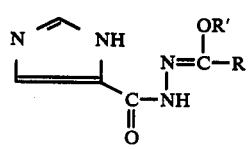

(II)

wherein R' is methyl or ethyl and R is as hereinabove defined in a non-polar high boiling organic solvent at a temperature of 225°–275° C. for a period of time sufficient for a substantial degree of ring closure to occur, and thereafter alkylating resultant compound with an allyl halide to recover compound (I), above defined.

* * * * *